US012606517B2

(12) United States Patent
Ye et al.

(10) Patent No.: US 12,606,517 B2
(45) Date of Patent: Apr. 21, 2026

(54) IBUPROFEN ESTER DERIVATIVE AND EMULSION PREPARATION THEREOF

(71) Applicant: NANJING HERON PHARMACEUTICAL SCIENCE AND TECHNOLOGY CO., LTD., Jiangning District Nanjing (CN)

(72) Inventors: Hai Ye, Jiangning District Nanjing (CN); Wenliang Zhou, Jiangning District Nanjing (CN); Jialin Wang, Jiangning District Nanjing (CN); Ying Xu, Jiangning District Nanjing (CN); Tao Min, Jiangning District Nanjing (CN); Tian Lv, Jiangning District Nanjing (CN); Xingran Chen, Jiangning District Nanjing (CN)

(73) Assignee: NANJING HERON PHARMACEUTICAL SCIENCE AND TECHNOLOGY CO., LTD., Nanjing (CN)

( * ) Notice: Subject to any disclaimer, the term of this patent is extended or adjusted under 35 U.S.C. 154(b) by 1149 days.

(21) Appl. No.: 17/624,188

(22) PCT Filed: Jun. 29, 2021

(86) PCT No.: PCT/CN2021/102989

§ 371 (c)(1),
(2) Date: Dec. 30, 2021

(87) PCT Pub. No.: WO2023/272472

PCT Pub. Date: Jan. 5, 2023

(65) Prior Publication Data

US 2023/0126556 A1 Apr. 27, 2023

(51) Int. Cl.

| | |
|---|---|
| ***A01N 37/00*** | (2006.01) |
| ***A01N 25/00*** | (2006.01) |
| ***A01N 37/12*** | (2006.01) |
| ***A01N 37/44*** | (2006.01) |
| ***A61K 9/107*** | (2006.01) |
| ***A61K 31/215*** | (2006.01) |
| ***A61K 31/24*** | (2006.01) |
| ***A61K 47/02*** | (2006.01) |
| ***A61K 47/10*** | (2017.01) |
| ***A61K 47/12*** | (2006.01) |
| ***A61K 47/24*** | (2006.01) |
| ***A61K 47/44*** | (2017.01) |
| ***C07C 68/06*** | (2020.01) |
| ***C07C 69/96*** | (2006.01) |

(52) U.S. Cl.

CPC .............. *C07C 69/96* (2013.01); *A61K 9/107* (2013.01); *A61K 47/02* (2013.01); *A61K 47/10* (2013.01); *A61K 47/12* (2013.01); *A61K 47/24* (2013.01); *A61K 47/44* (2013.01); *C07C 68/06* (2013.01)

(58) Field of Classification Search

None

See application file for complete search history.

(56) References Cited

U.S. PATENT DOCUMENTS

| | | | |
|---|---|---|---|
| 4,851,426 | A | 7/1989 | Ladkani et al. |
| 2023/0000812 | A1 | 1/2023 | Ye et al. |

FOREIGN PATENT DOCUMENTS

| | | | |
|---|---|---|---|
| CN | 101253148 | A | 8/2008 |
| CN | 102336714 | A | 2/2012 |
| CN | 103003228 | A | 3/2013 |
| CN | 103622907 | A | 3/2014 |
| CN | 104546706 | A | 4/2015 |
| CN | 105017157 | A | 11/2015 |
| CN | 110339165 | A | 10/2019 |
| CN | 114728883 | A | 7/2022 |
| EP | 0112130 | A1 | 6/1984 |
| JP | S59112944 | A | 6/1984 |
| JP | 2014523911 | A | 9/2014 |
| JP | 2020509005 | A | 3/2020 |
| KR | 20220024171 | A | 3/2022 |
| WO | 2011017634 | A2 | 2/2011 |
| WO | 2020101543 | A1 | 5/2020 |
| WO | 2022033202 | A1 | 2/2022 |

OTHER PUBLICATIONS

International Search Report for PCT/CN2021/102989, 6 pages, dated Mar. 31, 2022. [With English translation.].

Ben-Shabat, S , et al., "Synthesis of Pendent Carbonate Ester Groups onto Aliphatic Polycarbonates", Journal of Bioactive and Compatible Polymers 21, 385-397 (2006).

European Search Report , for EP Application No. 21824459.8, 6 pages, dated Jun. 16, 2023.

Murtha, J , et al., "Synthesis of the Cholesteryl Ester Prodrugs Cholesteryl Ibuprofen and Cholesteryl Flufenamate and Their Formulation into Phospholipid Microemulsions", Journal of Pharmaceutical Sciences 83 (9), 1222-1228 (1994).

CN Office Action , for CN Application No. 202180006417.7, 20 pages, dated Aug. 31, 2023. [with English translation].

JP Office Action , for JP Application No. 2021-577867, 6 pages dated Sep. 13, 2023. [Translation].

(Continued)

*Primary Examiner* — Layla Soroush

(74) *Attorney, Agent, or Firm* — Kilpatrick Townsend & Stockton LLP

(57) ABSTRACT

The application related to an ibuprofen ester derivative and an emulsion preparation thereof. A carboxyl group of racemic ibuprofen or S-ibuprofen is derivatized so that Compound N9 and a dextrorotatory enantiomer N9(S) thereof are obtained and further prepared into an emulsion preparation, which overcomes the problems of safety and compliance of patients existing in clinical application of existing ibuprofen/dexibuprofen injections and achieves the purposes of reducing vascular irritation, increasing clinical use approaches, and improving the stability of preparations in clinical applications.

12 Claims, 5 Drawing Sheets

(56) References Cited

OTHER PUBLICATIONS

KR Office Action , for KR Application No. 10-2021-7037584, 8 pages, dated Oct. 31, 2023. [Translation].

Yao, Y , et al., "Synthesis of Cefpodoxime Proxetil", Chinese Journal of Pharmaceuticals 39(2), 90-92 (2008). [English Abstract].

Chinese Search Report, for CN Application No. 2021800064177, 5 pages, dated Jul. 8, 2024.

IBUPROFEN ESTER DERIVATIVE AND EMULSION PREPARATION THEREOF

TECHNICAL FIELD

The present application belongs to the field of pharmaceutical preparations and, in particular, relates to an ibuprofen ester derivative and an emulsion preparation thereof.

BACKGROUND

Ibuprofen is a nonsteroidal anti-inflammatory drug of an arylpropionic acid class and was first marketed in the UK in 1968. Ibuprofen is a non-selective cyclooxygenase inhibitor and produces analgesic and anti-inflammatory effects by inhibiting cyclooxygenase and reducing the synthesis of prostaglandins; and plays an antipyretic role through hypothalamic thermoregulation center. Due to good anti-inflammatory, analgesic and antipyretic effects and few adverse reactions, ibuprofen is considered to be one of the safest nonsteroidal anti-inflammatory drugs (NSAIDs) and has been widely put into clinical use. Among them, ibuprofen injection, the first intravenous injection preparation of ibuprofen for treating pain and fever, was developed by Cumberland Pharmaceutical Co., Ltd. and approved for marketing in 2009.

However, ibuprofen injection has some problems in clinical use.

1. Since ibuprofen compound itself has a certain vascular irritation, it must be diluted to 4 mg/mL or lower before clinical use. However, there are still reports of phlebitis in patients at this low dose concentration, and the compliance of patients is poor.
2. Ibuprofen injection uses arginine as a solubilizer, and ibuprofen is easy to precipitate when diluted in clinical use, which is not conducive to the safety of clinical application.
3. In clinical use, ibuprofen injection can only be administered through infusion with an infusion time of greater than 30 minutes rather than intravenous pushing injection, which greatly limits its clinical application of defervescence.
4. Commercially available ibuprofen injection has a relatively high pH and opioids represented by morphine hydrochloride are easy to precipitate in the alkaline environment in the combination of PCA, which limits realizing the effects of combination of ibuprofen injection with opioids for reducing the dosage of opioids.

Ibuprofen contains a chiral carbon in structure. The commonly used ibuprofen in the market is racemic ibuprofen, which contains 50% levorotatory ibuprofen and 50% dextrorotatory ibuprofen (that is, S-ibuprofen). Studies have shown that levorotatory ibuprofen has weak anti-inflammatory, antipyretic and analgesic effects, and dextrorotatory ibuprofen has 28 times higher anti-inflammatory activity than levorotatory ibuprofen. Recent studies have shown that dextrorotatory ibuprofen, when used at only half the dosage of racemic ibuprofen, can obtain the same clinical efficacy, which can effectively reduce toxic and side effects. At present, dextrorotatory ibuprofen salt injections from a number of domestic pharmaceutical companies have been approved for clinical trial applications, but no mature injections have been clinically approved and marketed. Although the drug specification and the dosage of these rejections are reduced by replacing racemic compound with active dextroisomer, the safety problems of large vascular irritation and easy precipitation in clinical use have not been fundamentally solved.

SUMMARY

The present application provides an ibuprofen ester derivative and an emulsion preparation thereof.

In the present application, the carboxyl group of racemic ibuprofen or S-ibuprofen is derivatized so that Compound N9 and a dextrorotatory enantiomer N9(S) thereof are obtained and further prepared into an emulsion preparation, which overcomes the problems of safety and compliance of patients existing in the clinical application of existing ibuprofen/dexibuprofen injections and achieves the purposes of reducing vascular irritation, increasing clinical use approaches, and improving the stability of preparations in clinical applications.

In a first aspect, the present application provides an ibuprofen ester derivative, a racemate, stereoisomer, pharmaceutically acceptable salt or solvate thereof, or a solvate of a pharmaceutically acceptable salt thereof, where the ibuprofen ester derivative is a compound represented by Structural Formula (1):

Structural Formula (1)

N9

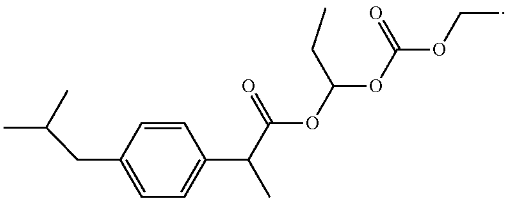

According to an embodiment of the present application, the compound represented by Structural Formula (1) is selected from a dextrorotatory enantiomer thereof, which is an isomer whose carbon at position 1 is in an S configuration and has the following structure:

N9(S)

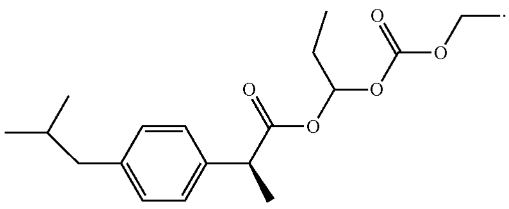

According to an embodiment of the present application, the dextrorotatory enantiomer N9(S) of the compound represented by Structural Formula (1) is a mixture of the following compounds N9(S)A and N9(S)B at any ratio:

N9(S)A

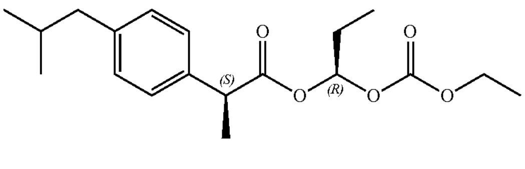

-continued

N9(S)B

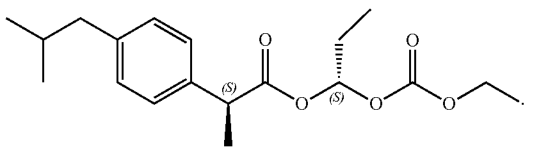

In a second aspect, the present application provides a method for preparing a compound represented by Structural Formula (1), a racemate, stereoisomer, pharmaceutically acceptable salt or solvate thereof, or a solvate of a pharmaceutically acceptable salt thereof. The method includes a step of reacting Compound 1 with a compound represented by Structural Formula (2):

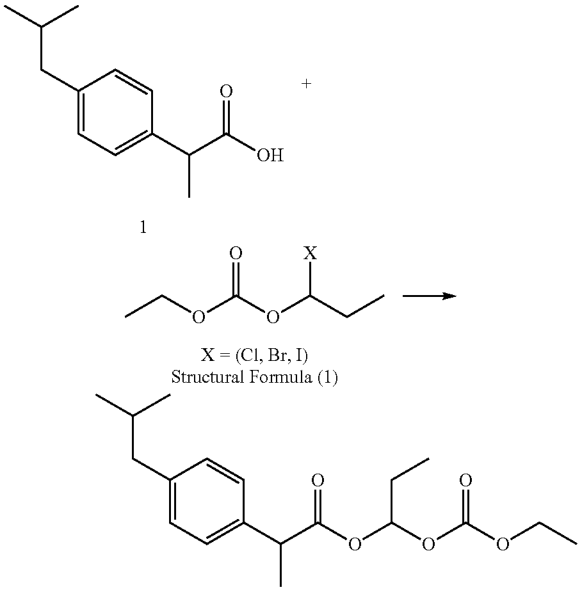

+

1

X = (Cl, Br, I)
Structural Formula (1)

Sturctural Formula (2)

wherein X denotes chlorine, bromine or iodine; and Compound 1 is racemic, S-configuration or R-configuration ibuprofen, that is, (±)-2-(4-isobutylphenyl)propionic acid, (S)-2-(4-isobutylphenyl)propionic acid or (R)-2-(4-isobutylphenyl)propionic acid.

According to an embodiment of the present application, the method for preparing the compound represented by Structural Formula (1) is conducted in the presence of an acid-binding agent.

According to an embodiment of the present application, the reaction temperature may be −5° C. to 80° C., and the reaction time may be 0.5-24 h; the acid-binding agent used may be one, two or more of inorganic bases such as NaOH, KOH, $K_2CO_3$, $KHCO_3$, $Na_2CO_3$ or $NaHCO_3$ or organic bases such as triethylamine, pyridine, DMAP, DIEA or DBU; and a reaction solvent may be one, two or more of acetone, dichloromethane, trichloromethane, carbon tetrachloride, tetrahydrofuran, toluene, ethyl acetate, acetonitrile, DMF, DMAc or ether.

In a third aspect, the present application further provides a method for preparing a halogenated organic carbonate represented by Structural Formula (2) (X is iodine). The method includes the following steps:

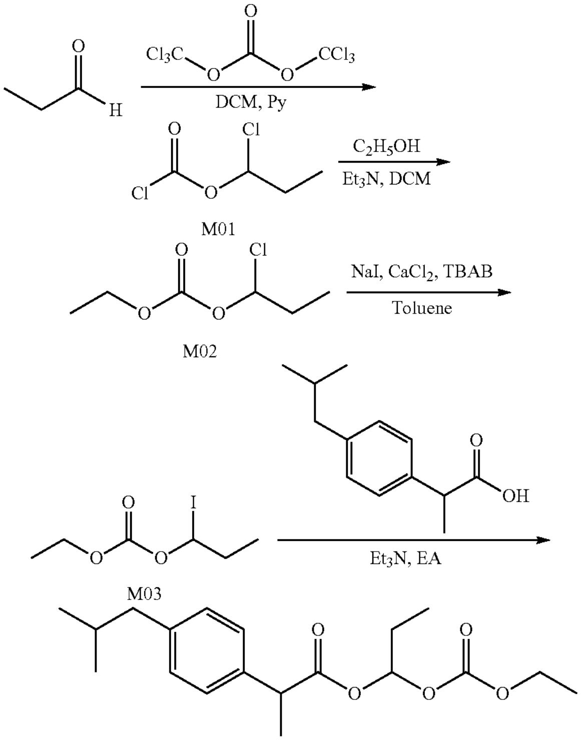

M01

M02

M03

N9 step 1: reacting triphosgene with n-propionaldehyde in an ice salt bath, using pyridine as a base and dichloromethane as a solvent, and finally distilling under reduced pressure to obtain M01;

step 2: reacting M01 with ethanol in an ice bath, using pyridine as a base and dichloromethane as a solvent, and finally distilling under reduced pressure to obtain M02;

step 3: mixing M02 with NaI, TBAB and calcium chloride for heating reaction, using toluene as a solvent, and finally distilling under reduced pressure to obtain M03; and step 4: reacting M03 with ibuprofen at room temperature, using triethylamine as a base and ethyl acetate as a solvent, and finally distilling under reduced pressure to obtain N9.

In a fourth aspect, the present application provides an application of a compound represented by the aforementioned Structural Formula (1), a racemate, stereoisomer, pharmaceutically acceptable salt or solvate thereof, or a solvate of a pharmaceutically acceptable salt thereof in preparation of a drug.

According to an embodiment of the present application, the drug may be used for treatment of one or more of the following diseases: rheumatoid arthritis, low back pain, migraine, neuralgia, periarthritis of shoulder, osteoarthritis, anti-inflammation and/or analgesia of neck-shoulder-wrist syndromes, analgesia and/or anti-inflammation after surgery, trauma or tooth extraction, and antipyretic and/or analgesia of acute upper respiratory tract inflammation.

According to an embodiment of the present application, the drug is a nonsteroidal anti-inflammatory drug.

In a fifth aspect, the present application further provides an emulsion preparation containing an ibuprofen ester derivative. The emulsion preparation includes:

(a) Compound N9 represented by Structural Formula (1), a racemate, stereoisomer, pharmaceutically acceptable salt or solvate thereof, or a solvate of a pharmaceutically acceptable salt thereof:

Structural Formula (1)

N9

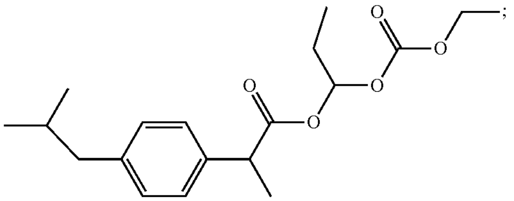

(b) an emulsifier and (c) oil.

According to an embodiment of the present application, based on a total weight of 100% of the emulsion preparation, a mass percentage of an active ingredient is 0.1-10%, preferably 5-10%.

According to an embodiment of the present application, the compound represented by Structural Formula (1) is selected from a dextrorotatory enantiomer thereof, which is an isomer whose carbon at position 1 is in an S configuration and has the following structure:

N9(S)

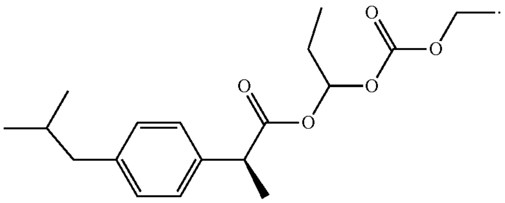

The emulsifier suitable for use in the present application is selected from lecithin and its derivatives, such as one, two or more of soybean lecithin, egg-yolk lecithin, hydrogenated lecithin, or saturated and unsaturated $C_{12-18}$ fatty acyl phosphatidylcholine; for example, egg-yolk lecithin and/or soybean lecithin.

According to an embodiment of the present application, the emulsifier is selected from egg-yolk lecithin and/or soybean lecithin and has a mass percentage of 0.5-15%, preferably 1.2-10%.

The oil suitable for use in the present application is an injectable oil ester, which is selected from soybean oil, safflower oil, cottonseed oil, olive oil, sesame oil, coconut oil, castor oil, sea buckthorn oil, evening primrose oil, corn oil, *Brucea javanica* oil, *perilla* oil, grape seed oil, tea oil, palm oil, peanut oil, medium chain oil (medium chain triglyceride), long chain triglyceride, ethyl oleate, acetylated monoglyceride, propylene glycol diester, glyceryl linoleate or polyethylene glycol glyceryl laurate, or a combination of two or more selected therefrom.

According to an embodiment of the present application, the oil is selected from one or more of sesame oil, median chain triglyceride, soybean oil, sunflower kernel oil or peanut oil and has a mass percentage of 0.1-15%, preferably 0.5-5%.

According to an embodiment of the present application, the emulsion preparation further includes a stabilizer, where the stabilizer is selected from oleic acid or/and sodium oleate and has a mass percentage of 0.01-1%.

According to an embodiment of the present application, the emulsion preparation further includes an isosmotic adjusting agent, where the isosmotic adjusting agent is selected from one or more of sucrose, glucose, sorbitol, xylitol, sodium chloride or glycerin.

According to an embodiment of the present application, the emulsion preparation further includes a pH adjusting agent, where the pH adjusting agent is selected from one or more of citric acid, hydrochloric acid, citric acid, fumaric acid, lysine, tartaric acid, histidine, sodium citrate, sodium hydroxide, sodium citrate, sodium dihydrogen phosphate or disodium hydrogen phosphate.

According to an embodiment of the present application, the emulsion preparation further includes a co-emulsifier, where the co-emulsifier is selected from one or more of Kolliphor HS15, polysorbate 80 or small-molecular alcohols such as ethanol and propylene glycol.

According to an embodiment of the present application, the emulsion preparation of the present application has an average particle size within a range of 10-1000 nm, for example, a range of 10-8M nm, a range of 10-550 nm, a range of 50-350 nm, a range of 50-200 nm, a range of 50-150 nm or the like.

In a sixth aspect, the present application further provides a method for preparing an emulsion preparation containing an ibuprofen ester derivative. The method includes the following steps:

(1) preparation of an oil phase: adding the ibuprofen ester derivative, an emulsifier and a stabilizer to oil, and shearing at a high speed to be uniformly mixed;

(2) preparation of a water phase: adding an isosmotic adjusting agent and a stabilizer to injectable water, adding a pH adjusting agent and a co-emulsifier when necessary, and stirring to dissolve;

(3) preparation of an initial emulsion: adding the oil phase in step (1) to the water phase in step (2), and shearing and dispersing at a high speed under water bath insulation to form the initial emulsion;

(4) preparation of a final emulsion: homogenizing the initial emulsion obtained in step (3) under a high pressure to obtain the final emulsion; and (5) filling with nitrogen, potting and sterilizing to obtain the emulsion preparation containing an ibuprofen ester derivative.

According to an embodiment of the present application, the emulsion preparation of the present application is a fat emulsion injection or a nanoemulsion injection.

The fat emulsion injection may be prepared by the method below.

The formulation amounts of oil phase and water phase are weighed respectively, the oil phase is sheared and dispersed with a high-speed disperser, and the water phase is subjected to magnetic stirring to be uniformly mixed. The water phase is warmed in a water bath of 60-65° C. and the oil phase is added to the water phase under the shear speed of 15000 rpm in a high-speed disperser. After complete addition, high-speed shearing is continued so that the initial emulsion is obtained. The initial emulsion is homogenized at a pressure of 800-860 bar for 3 cycles so that the final emulsions prepared with different emulsifiers are obtained. The obtained final emulsions are sterilized at 121° C. for 12 minutes. The prepared fat emulsion injection has an average particle size within a range of 100-550 nm, more preferably a range of 150-300 nm.

The nanoemulsion injection may be prepared by the method below:

The formulation amounts of oil phase and water phase are weighed respectively, the oil phase is sheared and dispersed with a high-speed disperser, and the water phase is subjected to magnetic stirring to be uniformly mixed. The water phase is warmed in a water bath of 60-65° C., and the water phase is added to the oil phase under the shear speed of 20000 rpm in a high-speed disperser. After complete addition, high-speed shearing is continued so that the initial emulsion is obtained. The initial emulsion is homogenized at a pressure of 800-860 bar for 3 cycles so that the final emulsions prepared with different emulsifiers are obtained. The obtained final emulsions are sterilized at 121° C. for 12 minutes or filtered using a filter membrane with a pore diameter of 0.22 μm to be sterilized. The prepared nanoemulsion injection has an average particle size within a range of 50-200 nm, more preferably a range of 50-150 nm.

The emulsion preparation prepared in the present application is suitable to be administered through parenteral administration, which includes intravenous, intraarterial, subcutaneous, intraperitoneal or intramuscular injection or infusion; or through intracranial administration, such as intrathecal or intracerebroventricular administration. The emulsion preparation may be administered parenterally in a single large bolus, or may be administered through, for example, a continuous infusion pump. Alternatively, the emulsion preparation may be administered intracranially such as intrathecally or intracerebroventricularly. Commonly used containers of injections include glass ampoules, vials, plastic ampoules, prefilled needles or the like.

The present application has the beneficial effects described below.

1. In the present application, the carboxyl group of racemic ibuprofen is derivatized so that Compound N9 and a dextrorotatory enantiomer N9(S) thereof are obtained, which overcomes the problems of ibuprofen injection such as short half-life, poor stability, irritation and easy precipitation in combined use. In vitro and in vivo plasma tests show that the compound of the present application has good pharmacokinetic properties. Further, the physical and chemical stability of the compound itself is relatively high. For example, the purity of the compound remains basically unchanged in a high temperature test (placed at 60° C. for 5-10 days).
2. The main pharmacological activity of ibuprofen is from dextrorotatory ibuprofen. In the present application, dextrorotatory ibuprofen is used as a raw material for directionally synthesizing a dextrorotatory ibuprofen ester derivative N9(S) in (IS) configuration. The by-products of dextrorotatory ibuprofen ester derivative N9(S) metabolism in human body are propionaldehyde and ethanol. The by-products are less toxic and have a faster metabolic rate at the same time. In addition, studies have found that N9(S) has a faster hydrolysis rate in plasma than N9(R) and can produce more dextrorotatory ibuprofen. It is known in the art that levorotatory ibuprofen has weak anti-inflammatory, antipyretic and analgesic effects, the efficacy of dextrorotatory ibuprofen (S configuration) is 28 times stronger than that of levorotatory ibuprofen (R configuration), and levorotatory ibuprofen may cause various adverse reactions such as gastrointestinal toxicity, water and sodium retention, decreased renal perfusion and allergic reactions. Therefore, it is of great significance to study and prepare the ibuprofen ester derivative in S configuration, that is, the dextrorotatory enantiomer of the compound represented by Structural Formula (1) in the present application.
3. In the present application, the physical and chemical properties of the active ingredient are studied, in vivo and in vitro metabolism tests of the active ingredient are comprehensively considered, and the formulation of a preparation of the active ingredient is further studied so that an efficient, safe and stable emulsion preparation containing the ibuprofen ester derivative is obtained. The test method of the present application can be used for preparing fat emulsion injection and nanoemulsion injection with good particle size distribution. The damages of nonsteroidal anti-inflammatory drugs such as traditional ibuprofen to gastrointestinal mucosae are avoided, thereby increasing the bioavailability of the drug.

DETAILED DESCRIPTION

Figure 1:
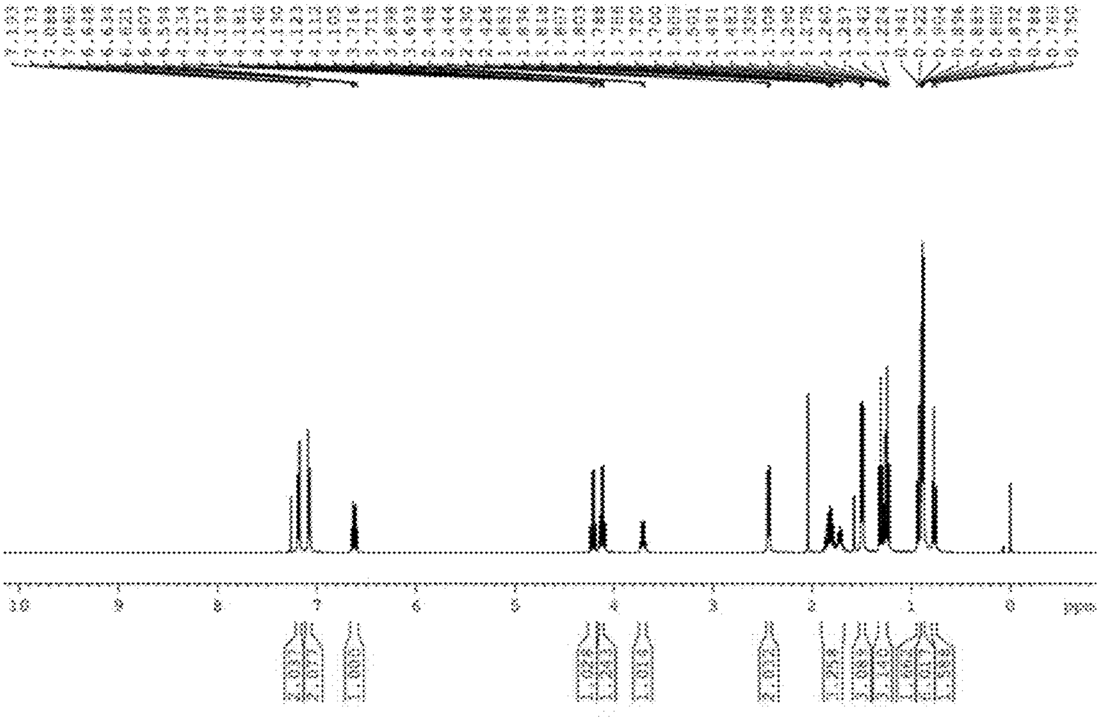
FIG. 1 shows an H NMR spectrum of Compound N9(S) of the present application.
Figure 2:
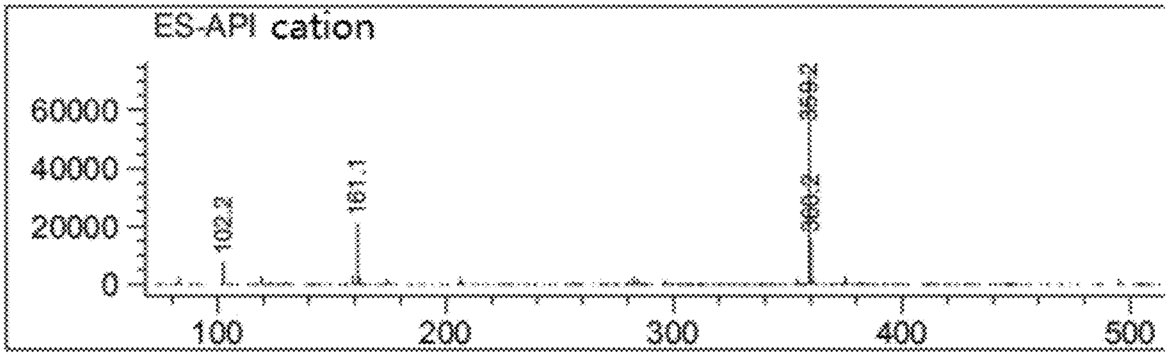
FIG. 2 shows a mass spectrum of Compound N9(S) of the present application.

The present application is further described in detail below in conjunction with specific examples and drawings. The following examples are only descriptive and not restrictive to limit the scope of the present application. Unless otherwise specified, all raw materials used are commercially available or self-made.

The main detection methods involved in the present application are as follows:

I. pH Determination

The pH is determined according to a pH determination method (Chinese Pharmacopoeia 2020 Edition General Rules 0631).

IL Determination of particle size and Zeta potential About 20 μL of emulsion injection is diluted in 10 mL of filtered and purified water and shook to be uniformly mixed so that a test mixture is obtained. According to a particle size determination method and a particle size distribution determination method (Chinese Pharmacopoeia 2020 Edition General Rules 0982 Third Method), the particle size and the Zeta potential are detected using a dynamic light scattering optical particle size analyzer PSS Nicomp Z3000 based on a Rayleigh scattering theory and using the following parameters: an optical intensity of 300 kHz, a refraction angle of 90°, a refractive index of 1.333, a viscosity of 0.933 cp and a time of 5 minutes. The Gaussian distribution diagram of the particle size is recorded, and data such as an average particle size, PI and Zeta potential are analyzed.

Example 1: Synthesis of Compound N9

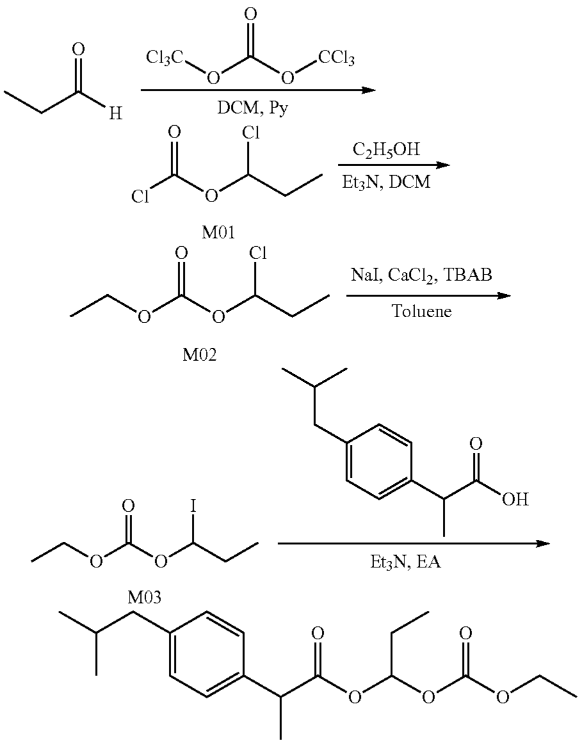

N9

Step 1: Triphosgene (1000.0 g, 3.37 mol) was weighed into a 5 L three-necked reaction flask, L of anhydrous dichloromethane was added, the reaction flask was purged three times with $N_2$ and transferred to a constant low-temperature reaction bath of −35° C., and the reaction solution was stirred continuously. The temperature of the reaction solution was controlled to be lower than −15° C., and Py (45.2 g, 0.57 mol) was measured and added dropwise to the reaction flask. The temperature of the reaction solution was controlled to be lower than −15° C., and n-propionaldehyde (460.2 g, 7.92 mol) was weighed and added dropwise to the reaction flask. After dropping, the temperature of the constant low-temperature reaction bath was set to −2° C. and maintained overnight. After directly distillation, 910.0 g of colorless oil was obtained with a yield of 73.2%.

Step 2: M01 (910.0 g, 5.80 mol) was weighed into a dry three-necked reaction flask. 10 mL of anhydrous DCM was added and stirred continuously, ethanol (400.2 g, 8.68 mol) was weighed and added to the above reaction flask. The reaction flask was transferred to a constant low-temperature reaction bath, and the reaction solution was stirred continuously. Triethylamine (720.0 g, 7.88 mmol) was weighed and added to the above reaction vessel. After dropping, the reaction flask was transferred to room temperature overnight. The reaction solution was suction-filtered, the filter cake was washed twice with 500 mL of dichloromethane, and the filtrate was washed with 5% $KHSO_4$ to a pH of 3-4, and then washed twice with 1.5 L of water, then washed with saturated brine, and dried with anhydrous sodium sulfate for 2 h. The resultant was concentrated under reduced pressure to obtain colorless oil, which was distilled so that 800.0 g of colorless oil was obtained with a yield of 83.1%.

Step 3: M02 (800.0 g, 4.8 mol), $CaCl_2$ (319.6 g, 2.9 mol) and TBAB (46.4 g, 50.8 mmol) were weighed into a 5 L three-necked reaction flask, 3.2 L of toluene was added, and NaI (1438.6 g, 9.6 mmol) was added and reacted for 1 h when the water bath was heated to 70° C. The reaction solution was suction-filtered, and the filtrate was washed with 1 L of water, added and washed with 1.6 L of 5% sodium thiosulfate aqueous solution, washed twice with 800 mL of water, washed with 800 mL of saturated brine, dried with an appropriate amount of anhydrous sodium sulfate, and concentrated to obtain yellow oil, which was distilled so that 720.2 g of light yellow oil was obtained.

Step 4: Ibuprofen (508.8 g, 2.47 mol) was weighed into a dry single-necked reaction flask, 10 mL ethyl acetate was added and stirred for ibuprofen to be dissolved, and 1-iodopropyl ethyl carbonate (720.2 g, 2.79 mol) was added. Then, diluted triethylamine (345.24 g, 3.4 mol) was slowly added dropwise to the reaction flask in an ice bath, and the reaction was transferred to 30° C. for reaction overnight. The reaction solution was suction-filtered, washed with 600 mL of water, washed with 600 mL of saturated brine, dried, and concentrated. After distillation, 513.4 g of light yellow oil, i.e., N9, was obtained.

$^1H$ NMR (400 MHz, $CDCl_3$) δ 7.19-7.07 (m, 411), 6.65-6.59 (m, 1H), 4.24-4.09 (m, 211), 3.73-3.68 (m, 11H), 2.45-2.43 (m. 2H), 1.89-1.68 (m, 3H), 1.51-1.48 (m, 3H), 1.33-1.23 (m, 3H), 0.94-0.75 (m, 9H):

ESI-MS m/z=359.2, $[M+Na]^+$.

Example 2: Synthesis of Compound N9(S)

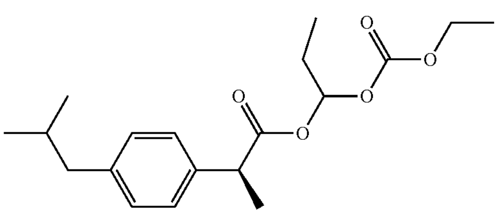

N9(S)

The test method was the same as that of EXAMPLE 1 except that ibuprofen was replaced with S-ibuprofen.

$^1H$ NMR (400 MHz, $CDCl_3$) δ 7.19-7.07 (m, 4H), 6.65-6.59 (m, 1H), 4.24-4.09 (m, 2H), 3.73-3.68 (m, 1H), 2.45-2.43 (m, 2H), 1.89-1.68 (m, 3H), 1.51-1.48 (m, 3H), 1.33-1.23 (m, 3H), 0.94-0.75 (m, 9H); ESI-MS m/z=359.2, $[M+Na]^+$.

Test Example 1: Study on the Stability of the Compound at a High Temperature

Test scheme: An appropriate amount of Compound N9 prepared in the present application was put in a vial and placed at a high temperature (60° C.) with light excluded. Samples were taken on Day 0, 5 and 10 respectively to investigate the purity of the compound and changes of the related substance (ibuprofen). The results are shown in Table 1.

TABLE 1

| Purity determination | | | | |
|---|---|---|---|---|
| | | Day 0 | Day 5 | Day 10 |
| N9 | Total purity (%) of a main peak (%) | 99.56 | 99.53 | 98.30 |
| | Ibuprofen (%) | / | / | 0.01 |

As can be seen from the test results, the compound of the present application has a purity of greater than 98% after 10 days of placement at a high temperature (60° C.) with light excluded, indicating good stability.

Test Example 2: Study on Metabolism of the Compound of the Present Application in Human Plasma A prodrug exerts efficacy through an original drug released through the enzymolysis of the prodrug in vivo. Therefore, the metabolic rate of the prodrug and the production rate in plasma are closely related to whether the prodrug can effectively exert efficacy and prolong a half-life.

In the present application, the conversion characteristics of Compound N9 and its isomers were evaluated by establishing an in vitro human plasma metabolism model. The test scheme was as follows:

(1) stock solutions (40 mM) of Compounds N9, N9(S) and N9(R) in pure acetonitrile were formulated respectively, and a stock solution (40 mM) of ibuprofen in pure acetonitrile was formulated;

(2) 25 μL stock solution of ibuprofen was mixed with 1 mL of human plasma and vortexed for 30 s. 200 μL sample was taken, added with 800 μL of acetonitrile to precipitate proteins and vortexed for 1 min, and then the reaction was terminated as an ibuprofen control; and the stock solutions (40 mM) of Compounds N9, N9(S) and N9(R) were diluted 200 times respectively as prodrug controls;

(4) 100 μL stock solutions of Compounds N9, N9(S) and N9(R) in pure acetonitrile were mixed with 4 mL of human plasma, respectively, vortexed for 30 s, and placed in an oscillating water bath heater with a constant temperature of 37° C. and oscillated at 200 rpm;

(5) 200 μL samples were taken at different time points (0, 15, 30, 60 and 120 min) with three samples at each time point, added with 800 μL of acetonitrile to precipitate proteins, vortexed for 1 min, and then the reaction was terminated; and a blank plasma control was obtained in the same manner;

(6) the samples were centrifuged at 12000 rpm for 10 min at 4° C., the supernatant was taken and injected at a volume of 30 μL (through a filter membrane), and changes of a peak area were recorded;

(7) The hydrolysis rates of Compounds N9, N9(S) and N9(R) were observed and analyzed. Compounds N9, N9(S) and N9(R) were metabolized in plasma for 120 min, and the test results are shown in Table 2.

TABLE 2

| Metabolism of Compounds N9, N9(S) and N9(R) | | |
|---|---|---|
| Compound | Remaining amount of a prodrug compound (%) | Amount of active metabolites produced (%) |
| N9 | 62.5 ± 1.3 | 20.3 ± 0.8 |
| N9(S) | 45.0 ± 2.1 | 36.2 ± 1.6 |
| N9(R) | 80.8 ± 5.9 | 12.9 ± 0.9 |

As can be seen from the test results, an S-isomer N9(S) of Compound N9 has a faster metabolic rate than the racemate N9, that is, dexibuprofen ester prodrug has a faster hydrolysis rate in plasma than racemic ibuprofen ester prodrug, and can be converted into active metabolites in human plasma more quickly than traditional racemic ibuprofen ester prodrug in vitro, so as to exert pharmacological activity.

Figure 3:
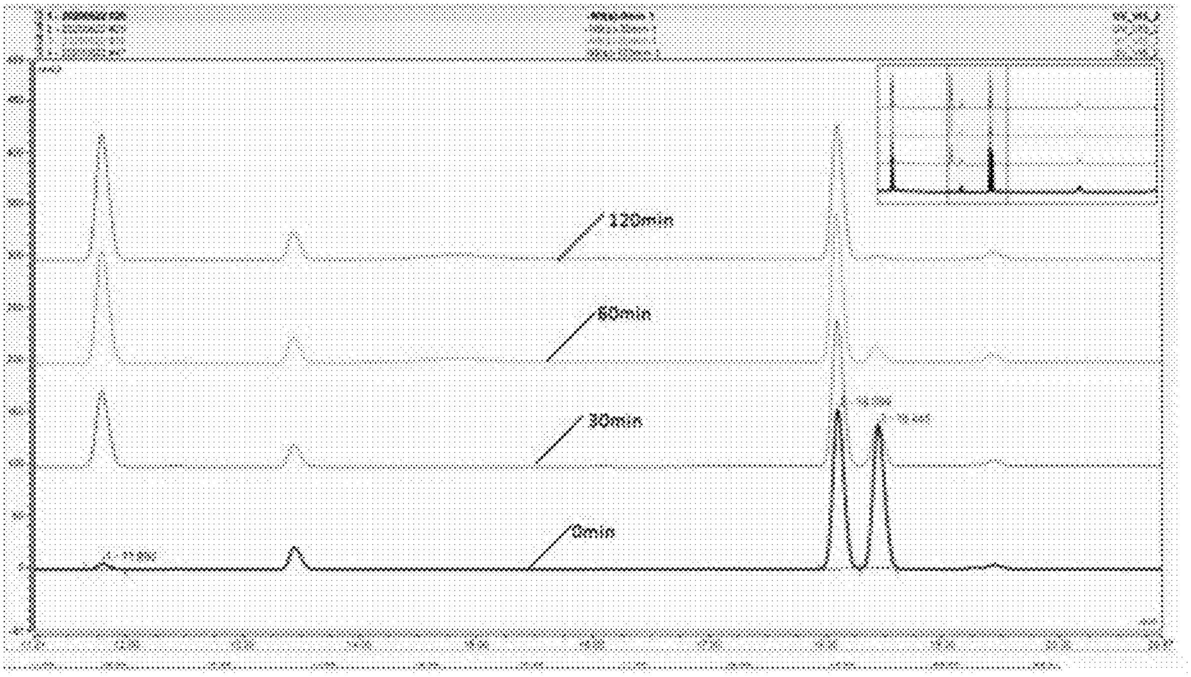
FIG. 3 shows a liquid chromatogram of degradation of Compound N9(S) of the present application in human plasma.

Meanwhile, inventors further discover during the study that Compound N9(S) contains two peaks, as shown in FIG. 3, which indicates that a dexibuprofen ester derivative, Compound N9(S), also includes a chiral center at the position where a side chain is joined in addition to a chiral center on main chain ibuprofen and two isomers of N9(S) are hydrolyzed at different rates by carboxylesterase in human plasma.

Test Example 3: Study on Pharmacokinetics of the Compound of the Present Application in Rats In the present application, after the dexibuprofen ester derivative N9(S) (solubilized by PEG400) and dexibuprofen (arginine salt solution) were administered to rats through tail vein injection at an equimolar dose, blood was taken from the fundus vein at 5, 10, 15, 30, 60, 120, 240, 360, 480 and 720 min after administration and put in test tubes treated with heparin. The whole blood was centrifuged at 8000 rpm for 5 min, and plasma samples were separated and stored at −80° C.

Figure 4:
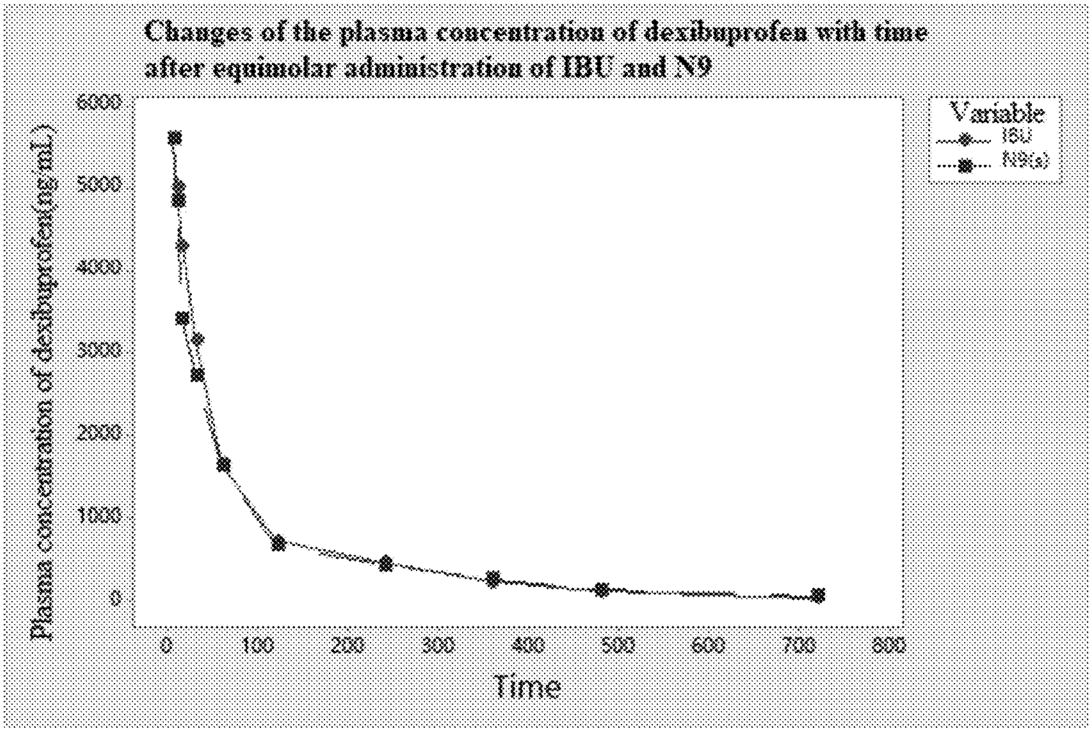
FIG. 4 shows plasma concentration-time curves of injection solutions of dexibuprofen and a dexibuprofen ester derivative N9(S).

The concentration of dexibuprofen (IBU) in plasma was analyzed and determined. Changes of dexibuprofen in rat plasma with time were investigated. FIG. 4 shows plasma concentration-time curves of dexibuprofen and dexibuprofen ester derivative N9(S) injections.

Through the analysis by pharmacokinetic software, the pharmacokinetic parameters were obtained, as shown in Table 4.

Preparation of test drug solutions: the volume of test drug solutions administered to rats through tail veins is 0.25 mL/100 g.

Dexibuprofen to be tested: an arginine solution of dexibuprofen containing dexibuprofen of 20 mg/mL was prepared: 200 μL of the solution was pipetted into a 10 mL EP tube, 4800 μL of normal saline was added into the tube with a dispensing gun, and the mixture was vortexed to be uniformly mixed, to obtain a dosing solution with a concentration of 0.8 mg/mL and a volume of 5 mL.

N9 to be tested: 20 mg dexibuprofen ester derivative N9 was weighed into a 15 mL EP tube, 10 mL of PEG400 was added into the tube with a dispensing gun, and the mixture was vortexed to be uniformly mixed, to obtain a PEG solution of the compound with a concentration of 2 mg/mL. 3250 μL PEG solution of N9 was pipetted into a 10 mL EP tube 1750 μL of normal saline was added into the tube with the dispensing gun, and the mixture was vortexed to be uniformly mixed, to prepare a dosing solution with a concentration of 1.3 mg/mL and a volume of 5 mL.

TABLE 3

| Administration scheme | | | | |
|---|---|---|---|---|
| Group | Test Substance | Molecular Weight g/mol | Dosage Ratio (Molar Mass Ratio) | Dosage (converted to rats) mg/kg |
| 1 | Dexibuprofen | 206.28 | 1 | 2 |
| 2 | N9 | 336.43 | 1.63 | 3.26 |

TABLE 4

| Pharmacokinetic parameters | | |
|---|---|---|
| Parameter | Dexibuprofen | N9S |
| $T_{1/2}$ (min) | 114.68 ± 15.54 | 145.98 ± 18.48 |
| $AUC_{0-t}$ (min*ng/mL) | 422847.52 ± 26422.43 | 385931.58 ± 46873.23 |
| Cl (mL/min/kg) | 4.70 ± 0.31 | 4.32 ± 0.93 |
| $MRT_{0-t}$ (min) | 122.61 ± 19.93 | 157.31 ± 16.67 |
| $V_{ss}$ (mL/kg) | 572.40 ± 65.75 | 1314.72 ± 227.31 |

As can be seen from the test results, the drug-time curve for the dexibuprofen ester derivative prodrug N9 which is converted into dexibuprofen in rats basically coincides with the drug-time curve for a dexibuprofen salt solution directly injected, and $AUC_{0-t}$, has no significant difference. It can be seen that the ester prodrug can be metabolized quickly into dexibuprofen with anti-inflammatory activity in rats, and the overall exposure in rats is consistent. The pharmacokinetic parameters show that the replacement of a dexibuprofen salt with an ester prodrug in injection preparations can prolong the half-life and mean residence time of dexibuprofen, reduce an elimination rate of dexibuprofen, and increase an apparent volume of distribution. Therefore, the present application prolongs the action time of the drug in vivo while achieving the same efficacy in clinical applications.

Test Example 4

Figure 5:
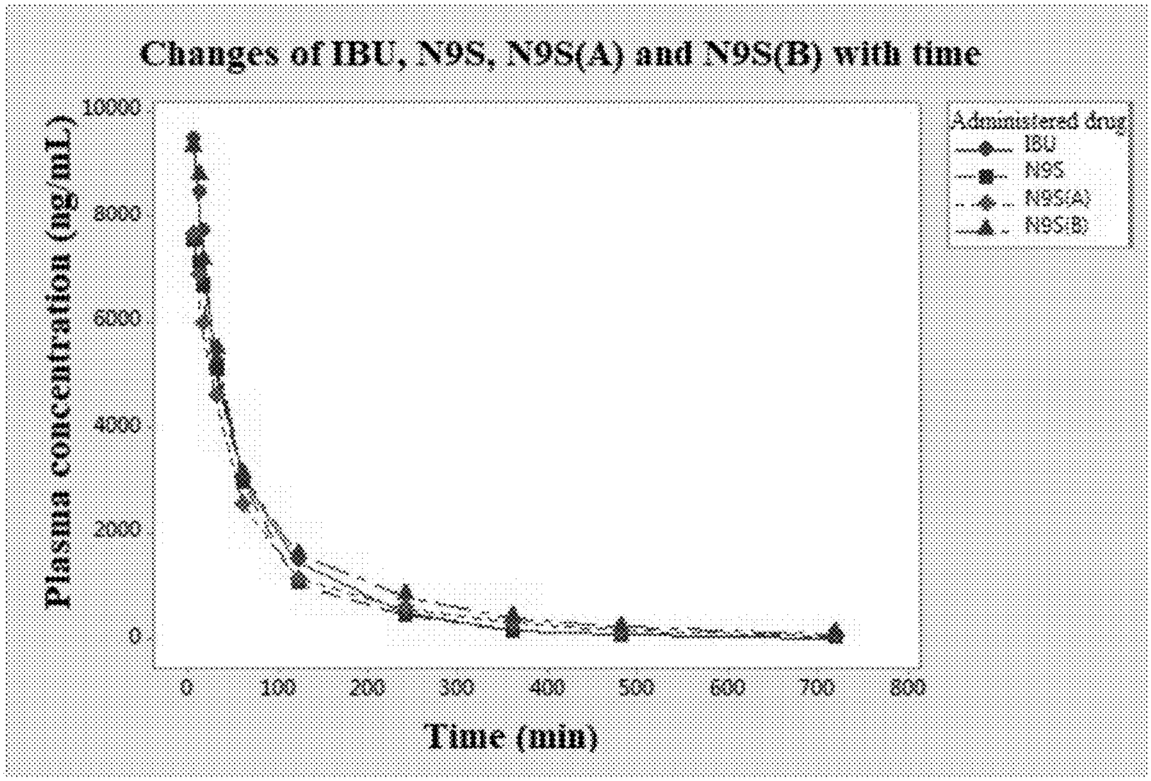
FIG. 5 shows plasma concentration-time curves of injection solutions of dexibuprofen, a dexibuprofen ester derivative N9(S) and side chain chiral compounds N9(S)A and N9(S)B.

The dexibuprofen derivative Compound N9(S) also includes a chiral center at the position where a side chain is joined in addition to a chiral center on main chain ibuprofen. Therefore, PEG400 solubilized solutions of a side chain racemic compound, side chain chiral compounds N9(S)A and N9(S)B of the dexibuprofen derivative Compound N9(S) and dexibuprofen (arginine saline solution) were administered through tail veins at an equimolar dose, and the changes of generation of dexibuprofen in rat plasma with time were monitored, so as to investigate differences in pharmacokinetics (prodrug conversion) between two side chain isomers of the main chain dextrorotatory esters. According to the analysis by pharmacokinetic software, FIG. 5 shows plasma concentration-time curves of injection solutions of dexibuprofen, the dexibuprofen ester derivative N9(S) and side chain chiral compound N9(S)A and N9(S)B.

Method for preparing test solutions: the dexibuprofen derivative Compound N9(S) (20 mg), a side chain isomer N9(S)A (20 mg) and a side chain isomer N9(S)B (20 mg) were each weighed into a 15 mL EP tube, 10 mL of PEG400 were added into the tubes with a dispensing gun respectively, and the mixture was vortexed to be uniformly mixed to obtain PEG solutions of the compounds with a concentration of 2 mg/mL. The PEG solution (3250 μL) of the test compound was pipetted into a 10 mL EP tube, 1750 μL of normal saline was added into the tube with the dispensing gun, and the mixture was vortexed to be uniformly mixed to obtain a dosing solution with a concentration of 1.3 mg/mL and a volume of 5 mL.

Method for preparing dexibuprofen: an arginine solution of dexibuprofen containing dexibuprofen of 20 mg/mL was prepared; 200 μL of the solution was pipetted into a 10 mL EP tube, 4800 μL of normal saline was added into the tube with a dispensing gun, and the mixture was vortexed to be uniformly mixed to obtain a dosing solution with a concentration of 0.8 mg/mL and a volume of 5 mL.

TABLE 5

| Administration scheme | | | | |
|---|---|---|---|---|
| No. | Abbreviation of Test compound | Dosing Solution | Dosage (mg/kg) | Volume of Administration through Tail Veins of Rats |
| Group 1 | N9(S) | PEG solution of N9(S) diluted with normal saline | 3.26 | 0.25 mL/100 g |
| Group 2 | N9(S)A | PEG solution of N9(S)A diluted with normal saline | 3.26 | 0.25 mL /100 g |
| Group 3 | N9(S)B | PEG solution of N9(S)B diluted with normal saline | 3.26 | 0.25 mL/100 g |
| Group 4 | Dexibuprofen | Arginine solution of dexibuprofen diluted with normal saline | 2 | 0.25 mL/100 g |

Compounds N9(S)A and N9(S)B are obtained through separation of Compound N9(S) with a reversed-phase C18 chromatographic column, which have the following specific structural formulas:

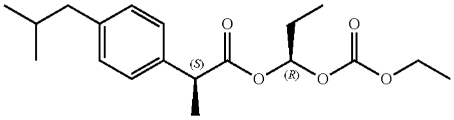

N9(S)A

TABLE 5-continued

| Administration scheme | | | | |
|---|---|---|---|---|
| No. | Abbreviation of Test compound | Dosing Solution | Dosage (mg/kg) | Volume of Administration through Tail Veins of Rats |
| 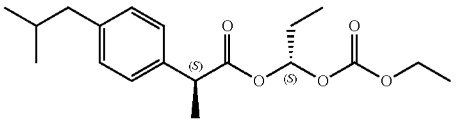 | | | | |

N9(S)B

The results of the pharmacokinetic study show that three test compounds of dexibuprofen can all be rapidly metabolized at an equimolar dose.

Test Example 5

Figure 6:
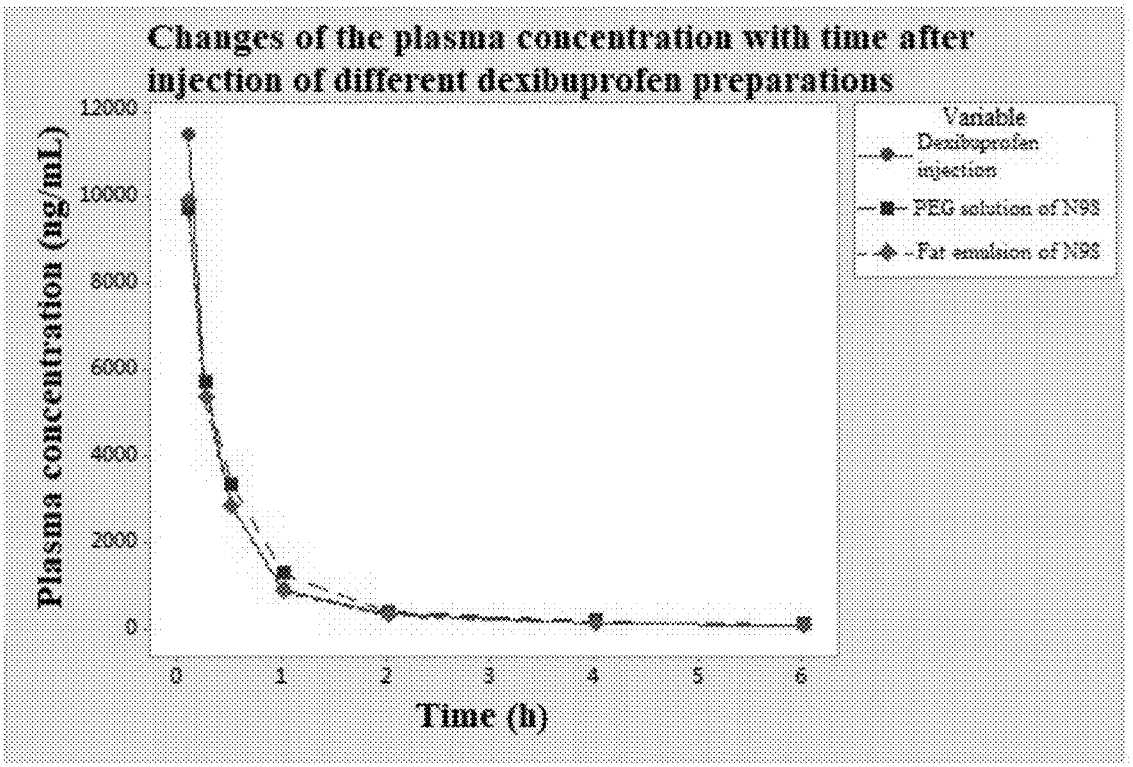
FIG. 6 shows plasma concentration-time curves of a PEG400 solubilized solution and an emulsion injection of a dexibuprofen derivative N9(S) and an arginine solution of dexibuprofen.
Figure 7:
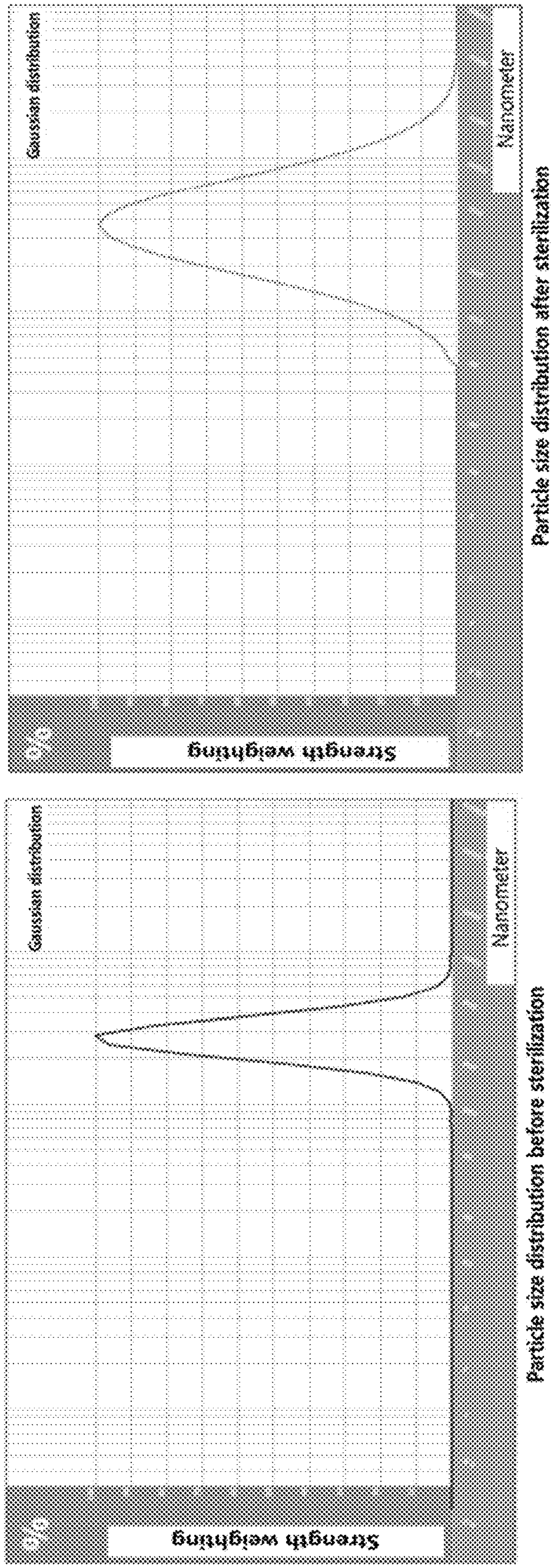
FIG. 7 shows particle size distribution diagrams of a fat emulsion preparation of the present application before and after sterilization.
Figure 8:
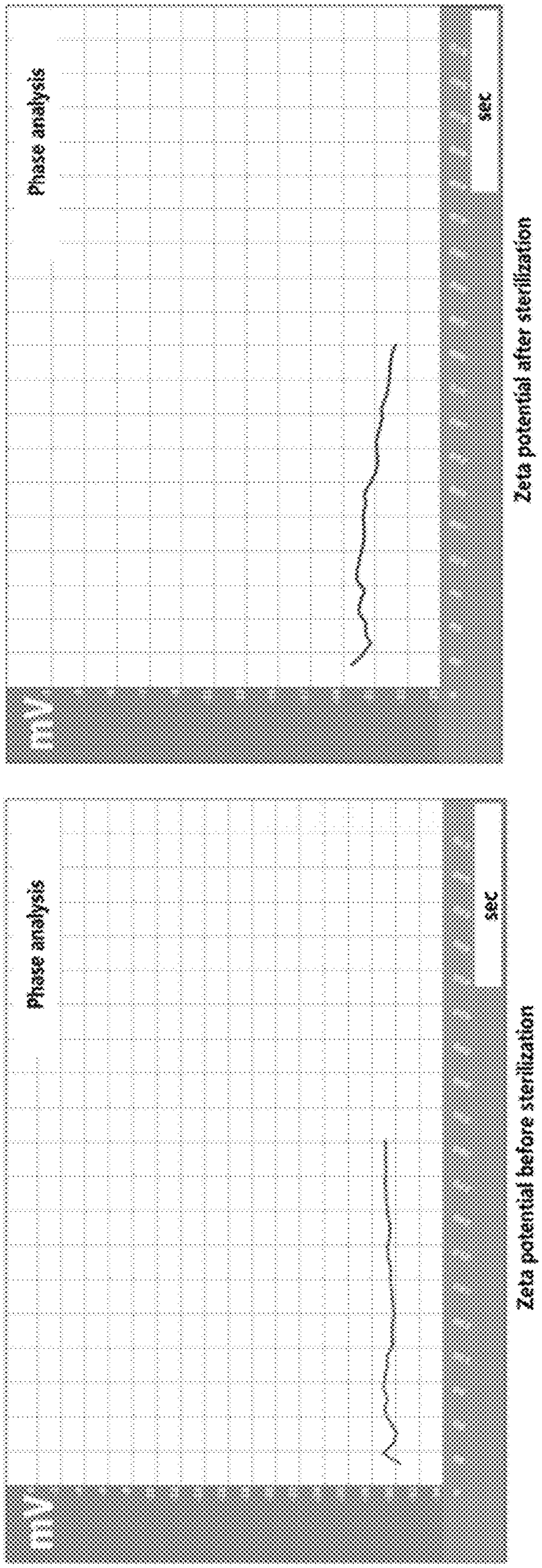
FIG. 8 shows Zeta potential determination results of a fat emulsion preparation of the present application before and after sterilization.

The dexibuprofen ester derivative N9(S) solubilized by PEG, the dexibuprofen ester derivative N9(S) using an emulsion injection (see follow-up Example 9) as a carrier and an arginine injection of dexibuprofen were administered through tail veins at an equimolar dose, and differences in pharmacokinetics for conversion into dexibuprofen in rat plasma was analyzed by pharmacokinetic software. FIG. 6 shows plasma concentration-time curves of the PEG400 solubilized solution and the emulsion injection of the dexibuprofen derivative N9(S) and the arginine solution of dexibuprofen.

TABLE 6

| Administration scheme | | | |
|---|---|---|---|
| Test Substance | Dose (mg/kg) | Concentration (mg/mL) | Volume of Administration (mL/kg) |
| Arginine solution of dexibuprofen | 2 | 0.8 | 0.25 mL/100 g |
| N9(S) (PEG + normal saline) | 3.26 | 1.3 | 0.25 mL/100 g |
| N9(S) (emulsion injection) | 3.26 | 1.3 | 0.25 mL/100 g |

Remarks: Among the preceding test substances, the solution of dexibuprofen ester derivative in PEG and normal saline was prepared for immediate use according to the administration concentration, and the emulsion injection and arginine solution were both diluted with normal saline to the required volume of administration.

Method for preparing the test solution of N9(S) (PEG+ normal saline): the dexibuprofen derivative Compound N9(S) (20 mg) was weighed into a 15 mL EP tube, 10 mL of PEG400 was added into the tube with a dispensing gun, and the mixture was vortexed to be uniformly mixed to prepare a PEG solution of the compound with a concentration of 2 mg/mL. The PEG solution (3250 μL) of the test compound was pipetted into a 10 mL EP tube, 1750 μL of normal saline was added into the tube with the dispensing gun, and the mixture was vortexed to be uniformly mixed to obtain a dosing solution with a concentration of 1.3 mg/mL and a volume of 5 mL.

Method for preparing the test solution of N9(S) (emulsion injection): an emulsion injection (215 μL) containing N9(S) compound (the content of which was 60 mg/mL) was added into a 15 mL EP tube and 10 mL of normal saline was added into the tube with a dispensing gun to obtain a dosing solution with a concentration of 1.3 mg/mL and a volume of 5 mL.

Method for preparing the arginine solution of dexibuprofen: 200 μL of the arginine solution of dexibuprofen containing dexibuprofen of 20 mg/mL was pipetted into a 10 mL EP tube, 4800 μL of normal saline was added into the tube with a dispensing gun, and the mixture was vortexed to be uniformly mixed to obtain a dosing solution with a concentration of 0.8 mg/mL and a volume of 5 mL.

The results of the pharmacokinetic study show that after the PEG400 solubilized solution and emulsion injection of the dexibuprofen ester derivative N9(S) and the arginine solution of dexibuprofen were administered through tail veins of rats at an equimolar dose, the drug-time curves of dexibuprofen in vivo basically coincide, indicating that the formulation of the emulsion injection has no significant effect on the release and conversion of the prodrug into the anti-inflammatory active substance.

Test Example 6: Oil Phase Screening

Emulsion injections were prepared using different oil. The composition of the formulation is shown in Table 7.

TABLE 7

| Formulation of the emulsion injection | | |
|---|---|---|
| Category | Reagent | Proportion (w/w %) |
| Oil phase | Egg-yolk lecithin | 1.2 |
| | N9(S) | 6 |
| | Oil | 6 |
| | Oleic acid | 0.5 |
| Water phase | Glycerin | 2.3 |
| | Disodium hydrogen phosphate | 0.023 |
| | Purified water | 83.977 |
| | Sodium oleate | 0.02 |

The oil is selected from peanut oil, medium chain triglyceride, rice oil, castor oil, sunflower kernel oil, sesame oil, sunflower kernel oil, tea oil, corn germ oil and soybean oil.

Test Method:

The formulation amounts of oil phase and water phase were weighed respectively, the oil phase was sheared for 10 min with a high-speed disperser, and the water phase was subjected to magnetic stirring to be uniformly mixed. The water phase was warmed in a water bath of 65° C., and the oil phase was added to the water phase under the shear speed of 15-0.0 rpm in a high-speed disperser. After complete addition, high-speed shearing was continued for 10 min so that an initial emulsion was obtained. The initial emulsion was homogenized at a pressure of 800-860 bar for 3 cycles so that final emulsions prepared with different oil were obtained. The obtained final emulsions were sterilized at 121° C. for 12 minutes. The average particle size, Zeta potential and PI of the final emulsion were determined.

TABLE 8

| Determination of the average particle size, Zeta potential and PI | | | | | | | |
|---|---|---|---|---|---|---|---|
| | | Before Sterilization | | | After Sterilization | | |
| Example | Oil Phase | Average Particle Size (nm) | Zeta (mV) | PI | Average Particle Size (nm) | Zeta (mV) | PI |
| 1 | Peanut oil | 246.04 ± 83.90 | −32.23 | 0.12 | 264.03 ± 18.22 | −30.50 | 0.00 |
| 2 | Medium chain triglyceride | 242.28 ± 142.67 | −32.82 | 0.35 | 277.24 ± 79.29 | −28.85 | 0.08 |
| 3 | Rice oil | 274.36 ± 158.31 | −30.63 | 0.33 | 275.63 ± 122.10 | −26.05 | 0.20 |
| 4 | Castor oil | 328.74 ± 234.39 | −30.56 | 0.51 | 340.33 ± 113.67 | −26.74 | 0.11 |
| 5 | Sesame oil | 247.84 ± 22.31 | −30.97 | 0.01 | 254.42 ± 10.69 | −29.92 | 0.00 |
| 6 | Sunflower kernel oil | 251.62 ± 20.63 | −28.18 | 0.01 | 253.33 ± 25.08 | −25.94 | 0.01 |
| 7 | Tea oil | 262.69 ± 35.99 | −27.44 | 0.02 | 262.65 ± 90.88 | −22.09 | 0.12 |
| 8 | Corn germ oil | 239.22 ± 56.70 | −30.06 | 0.06 | 236.84 ± 108.71 | −29.84 | 0.21 |
| 9 | Soybean oil | 234.40 ± 31.64 | −33.63 | 0.02 | 336.21 ± 89.14 | −31.47 | 0.04 |

The above test results show that Examples 1, 2, 5, 6 and 9 have lower average particle sizes, greater absolute values of the Zeta potential and lower PI values so that the oil phase in the fat emulsion of the present application is preferably sesame oil, medium chain triglyceride, soybean oil, sunflower kernel oil or peanut oil. Considering that most of drug-loaded emulsion injections and nanoemulsions widely used in clinics at present use soybean oil as the oil phase to be added, the effect of the emulsion injection on the stability of the preparation is only investigated when using soybean as the oil phase in subsequent examples.

Test Example 7: Emulsifier Screening

Emulsion injections were prepared using different emulsifiers. The composition of the formulation is shown in Table 9.

TABLE 9

| Formulation of the emulsion injection | | |
|---|---|---|
| Category | Reagent | Proportion (w/w %) |
| Oil phase | Emulsifier | 1.2 |
| | N9(S) | 6 |
| | Soybean oil | 6 |
| | Oleic acid | 0.5 |

TABLE 9-continued

| Formulation of the emulsion injection | | |
|---|---|---|
| Category | Reagent | Proportion (w/w %) |
| Water phase | Glycerin | 2.3 |
| | Disodium hydrogen phosphate | 0.023 |
| | Purified water | 83.977 |
| | Sodium oleate | 0.02 |

The emulsifier is selected from natural egg-yolk lecithin, hydrogenated egg-yolk lecithin, natural soybean lecithin, hydrogenated soybean lecithin sphingomyelin and phosphatidylcholine.

Test Method

The formulation amounts of oil phase and water phase were weighed respectively, the oil phase was sheared for 10 min with a high-speed disperser IKA T10, and the water phase was subjected to magnetic stirring to be uniformly mixed. The water phase was warmed in a water bath of 65° C., and the oil phase was added to the water phase under the shear speed of 15000 rpm in a high-speed disperser IKA T25. After complete addition, high-speed shearing was continued for 10 min so that an initial emulsion was obtained. The initial emulsion was homogenized at a pressure of 800-460 bar for 3 cycles so that final emulsions prepared with different emulsifiers were obtained. The obtained final emulsions were sterilized at 121° C. for 12 minutes. The average particle size, Zeta potential and PI of the final emulsion were determined.

TABLE 10

| Determination of the average particle size, Zeta potential and PI | | | | | | | |
|---|---|---|---|---|---|---|---|
| | | Before Sterilization | | | After Sterilization | | |
| Example | Emulsifier | Average Particle Size (nm) | Zeta (mV) | PI | Average Particle Size (nm) | Zeta (mV) | PI |
| 10 | Egg-yolk lecithin | 242.16 ± 34.22 | −33.06 | 0.03 | 281.14 ± 46.76 | −31.59 | 0.03 |
| 11 | Hydrogenated egg-yolk lecithin | 321.16 ± 292.49 | −23.18 | 0.57 | 369.93 ± 308.25 | −19.90 | 0.64 |
| 12 | Natural soybean lecithin | 265.98 ± 49.02 | −31.83 | 0.05 | 291.68 ± 57.79 | −30.44 | 0.07 |
| 13 | Hydrogenated soybean lecithin | 290.23 ± 67.54 | −30.27 | 0.11 | 322.85 ± 84.01 | −27.51 | 0.14 |
| 14 | Sphingomyelin | 403.22 ± 250.29 | −26.10 | 0.51 | 457.30 ± 284.58 | −22.59 | 0.59 |
| 15 | Phosphatidylcholine | 319.86 ± 112.13 | −28.18 | 0.40 | 356.35 ± 145.61 | −26.06 | 0.44 |

The above test results show that Examples 10 and 12 have lower average particle sizes, greater absolute values of the Zeta potential and lower PI values so that the emulsifier in the fat emulsion of the present application is preferably egg-yolk lecithin and natural soybean lecithin. Considering that most of drug-loaded emulsion injections and nanoemulsions widely used in clinics at present use natural egg-yolk lecithin as the emulsifier to be added, the effect of the emulsion injection on the stability of the preparation is only investigated using natural egg-yolk lecithin as the emulsifier in subsequent examples.

Test Example 8: Screening of an Amount of the Emulsifier

Emulsion injections were prepared using different amounts of the emulsifier. The composition of the formulation is shown in Table 11.

TABLE 11

| Formulation of the emulsion injection | | |
|---|---|---|
| Category | Reagent | Proportion (w/w %) |
| Oil phase | Emulsifier | See the test method |
| | N9(S) | 6 |
| | Soybean oil | 6 |
| | Oleic acid | 0.5 |
| Water phase | Glycerin | 2.3 |
| | Disodium hydrogen phosphate | 0.023 |
| | Purified water | 83.977 |

The emulsifier is natural egg-yolk lecithin and used in an amount of 0.5% to 15%.

Test Method for Examples 16 to 18

The formulation amounts of oil phase and water phase were weighed respectively, the oil phase was sheared for 10 min with a high-speed disperser IKA T10, and the water phase was subjected to magnetic stirring to be uniformly mixed. The water phase was warmed in a water bath of 65° C., and the oil phase was added to the water phase under the shear speed of 15000 rpm in a high-speed disperser IKA T25. After complete addition, high-speed shearing was continued for 10 min so that an initial emulsion was obtained. The initial emulsion was homogenized at a pressure of 800-860 bar for 3 cycles so that final emulsions prepared with different emulsifiers were obtained. The obtained final emulsions were sterilized at 121° C. for 12 minutes. The average particle size, Zeta potential and PI of the final emulsion were determined.

TABLE 12

Determination of the average particle size, Zeta potential and PI

| Example | Proportion of Natural Egg-yolk Lecithin (w/w %) | Before Sterilization Average Particle Size (nm) | Before Sterilization Zeta (mV) | Before Sterilization PI | After Sterilization Average Particle Size (nm) | After Sterilization Zeta (mV) | After Sterilization PI |
|---|---|---|---|---|---|---|---|
| 16 | 0.5 | 323.27 ± 187.67 | −19.69 | 0.28 | 367.53 ± 134.57 | −16.33 | 0.34 |
| 17 | 1.2 | 232.19 ± 58.92 | −33.10 | 0.06 | 248.23 ± 65.25 | −31.23 | 0.07 |
| 18 | 5.0 | 210.56 ± 79.23 | −36.65 | 0.08 | 223.79 ± 86.58 | −35.74 | 0.10 |

Test Method for Examples 19 and 20

The formulation amounts of oil phase and water phase were weighed respectively, the oil phase was sheared for 10 min with a high-speed disperser IKA T10, and the water phase was subjected to magnetic stirring to be uniformly mixed. The water phase was warmed in a water bath of 60° C., and the water phase was added to the oil phase under the shear speed of 20000 rpm in a high-speed disperser IKA T25. After complete addition, high-speed shearing was continued for 3 min so that an initial emulsion was obtained. The initial emulsion was homogenized at a pressure of 800-860 bar for 3 cycles so that final emulsions prepared with different emulsifiers were obtained. The obtained final emulsions were sterilized at 121° C. for 12 minutes or filtered using a filter membrane with a pore diameter of 0.22 μm to be sterilized. The average particle size, Zeta potential and PI of the final emulsion were determined.

TABLE 13

Determination of the average particle size, Zeta potential and PI

| | | | | | After Sterilization | | | | | |
|---|---|---|---|---|---|---|---|---|---|---|
| | Proportion of Natural | Before Sterilization | | | High Temperature Sterilization | | | Sterilization through Filtration | | |
| Example | Egg-yolk lecithin (w/w %) | Average Particle Size (nm) | Zeta (mV) | PI | Average Particle Size (nm) | Zeta (mV) | PI | Average Particle Size (nm) | Zeta (mV) | PI |
| 19 | 10.0 | 167.34 ± 65.47 | −36.76 | 0.15 | 188.23 ± 87.54 | −34.78 | 0.22 | 143.23 ± 43.53 | −35.65 | 0.12 |
| 29 | 15.0 | 176.78 ± 86.23 | −42.36 | 0.28 | 187.94 ± 88.78 | −41.43 | 0.34 | 155.23 ± 56.58 | −43.53 | 0.19 |

The above test results show that Examples 7, 18 and 19 have lower average particle sizes and higher Zeta potentials so that the amount of natural egg-yolk lecithin in the present application is preferably 1.2-10%.

Test Example 9: Screening of an Amount of Soybean Oil

Emulsion injections were prepared using different amounts of the emulsifier. The composition of the formulation is shown in Table 14.

TABLE 14

Formulation of the emulsion injection

| Category | Reagent | Proportion (w/w %) |
|---|---|---|
| Oil phase | Emulsifier | 1.2 |
| | N9(S) | 6 |
| | Soybean oil | See the test method |
| | Oleic acid | 0.5 |
| Water phase | Glycerin | 2.3 |
| | Disodium hydrogen phosphate | 0.023 |

TABLE 14-continued

Formulation of the emulsion injection

| Category | Reagent | Proportion (w/w %) |
|---|---|---|
| | Purified water | 83.977 |
| | Sodium oleate | 0.02 |

Soybean oil is used in an amount of 0% to 15%.

Test Method for Examples 21 and 22

The formulation amounts of oil phase and water phase were weighed respectively, the oil phase was sheared for 10 min with a high-speed disperser IKA T10 and the water phase was subjected to magnetic stirring to be uniformly mixed. The water phase was warmed in a water bath of 60° C., and the water phase was added to the oil phase under the shear speed of 20000 rpm in a high-speed disperser IKA T25. After complete addition high-speed shearing was continued for 3 min so that an initial emulsion was obtained. The initial emulsion was homogenized at a pressure, of 8004-~60 bar for 3 cycles so that final emulsions prepared with different emulsifiers were obtained. The obtained final emulsions were sterilized at 121° C. for 12 minutes or filtered using a filter membrane with a pore diameter of 0.22 μm to be sterilized. The average particle size. Zeta potential and PI of the final emulsion were determined.

TABLE 15

Determination of the average particle size, Zeta potential and PI

| | | Before Sterilization | | | After Sterilization: High Temperature Sterilization | | | After Sterilization: Sterilization through Filtration | | |
|---|---|---|---|---|---|---|---|---|---|---|
| Example | Proportion of soybean oil (w/w %) | Average Particle Size (nm) | Zeta (mV) | PI | Average Particle Size (nm) | Zeta (mV) | PI | Average Particle Size (nm) | Zeta (mV) | PI |
| 21 | 0 | 254.58 ± 76.89 | −26.67 | 0.25 | 276.73 ± 89.04 | −20.09 | 0.28 | 222.03 ± 67.80 | −28.05 | 0.22 |
| 22 | 0.5 | 184.23 ± 65.24 | −32.23 | 0.24 | 197.98 ± 77.65 | −26.87 | 0.29 | 158.23 ± 45.67 | −33.23 | 0.23 |
| 23 | 1.2 | 200.03 ± 56.53 | −33.65 | 0.15 | 232.32 ± 77.65 | −27.89 | 0.18 | 157.98 ± 43.23 | −35.89 | 0.09 |

Test Method for Examples 23 to 25

The formulation amounts of oil phase and water phase were weighed respectively, the oil phase was sheared for 10 min with a high-speed disperser IKA T10, and the water phase was subjected to magnetic stirring to be uniformly mixed. The water phase was warmed in a water bath of 65° C., and the oil phase was added to the water phase under the shear speed of 15000 rpm in a high-speed disperser IKA T25. After complete addition, high-speed shearing was continued for 10 min so that an initial emulsion was obtained. The initial emulsion was homogenized at a pressure of 800-860 bar for 3 cycles so that final emulsions prepared with different emulsifiers were obtained. The obtained final emulsions were sterilized at 121° C. for 12 minutes. The average particle size, Zeta potential and PI of the final emulsion were determined.

TABLE 16

Determination of the average particle size, Zeta potential and PI

| | | Before Sterilization | | | After Sterilization | | |
|---|---|---|---|---|---|---|---|
| Example | Proportion of soybean oil (w/w %) | Average Particle Size (nm) | Zeta (mV) | PI | Average Particle Size (nm) | Zeta (mV) | PI |
| 24 | 5 | 245.87 ± 87.56 | −27.89 | 0.21 | 276.37 ± 72.54 | −24.98 | 0.24 |
| 25 | 10 | 298.87 ± 89.78 | −25.54 | 0.35 | 338.76 ± 108.56 | −22.56 | 0.40 |
| 26 | 15 | 387.56 ± 123.79 | −20.19 | 0.42 | 401.49 ± 165.74 | −17.89 | 0.45 |

The above test results show that Examples 21, 22 and 23 have lower average particle sizes and higher Zeta potentials so that the amount of soybean oil in the present application is preferably 0.5-5%.

Examples 27 to 40

Emulsion injections were prepared using different proportions of API (N9(S)), oil, emulsifier, stabilizer, co-emulsifier, isosmotic adjusting agent and pH adjusting agent. The composition of the formulation is shown in Table 17.

Test Method:

(1) Preparation of an oil phase: an active ingredient N9(S), an emulsifier and a stabilizer were added to oil and sheared at a high speed to be uniformly mixed so that the oil phase was obtained.

(2) Preparation of a water phase: an isosmotic adjusting agent and a stabilizer were added to injectable water and stirred to be dissolved so that the water phase was obtained, where a pH adjusting agent and a co-emulsifier were added when necessary.

TABLE 17

Formulation of the emulsion injection

| Example | API | Oil | Emulsifier | Stabilizer | Co-emulsifier | Isosmotic Adjusting Agent | pH Adjusting Agent | Injectable Water |
|---|---|---|---|---|---|---|---|---|
| 27 | 0.1 g | Soybean oil/1.2 g | Natural egg-yolk lecithin/ 1.2 g | Oleic acid/0.5 g Sodium oleate/0.02 g | / | Glycerin/ 2.3 g | Disodium hydrogen phosphate/ 0.023 g | Added to a total weight of 100 g |
| 28 | 5 g | Soybean oil/1.2 g | Natural egg-yolk lecithin/ 1.2 g | Oleic acid/0.5 g Sodium oleate/0.02 g | / | Glycerin/ 2.3 g | Disodium hydrogen phosphate/ 0.023 g | Added to a total weight of 100 g |
| 29 | 10 g | Soybean oil/1.2 g | Natural egg-yolk lecithin/ 1.2 g | Oleic acid/0.5 g Sodium oleate/0.02 g | / | Glycerin/ 2.3 g | Disodium hydrogen phosphate/ 0.023 g | Added to a total weight of 100 g |
| 30 | 15 g | Soybean oil/1.2 g | Natural egg-yolk lecithin/ 1.2 g | Oleic acid/0.5 g Sodium oleate/0.02 g | / | Glycerin/ 2.3 g | Disodium hydrogen phosphate/ 0.023 g | Added to a total weight of 100 g |
| 31 | 5 g | Soybean oil/1.2 g | Natural egg-yolk lecithin/ 1.2 g | Oleic acid/0.5 g Sodium oleate/0.02 g | Propylene glycol | Glycerin/ 2.3 g | Tartaric acid, histidine/ appropriate amount | Added to a total weight of 100 g |
| 32 | 5 g | Soybean oil/1.2 g | Natural egg-yolk lecithin/ 1.2 g | Oleic acid/0.5 g Sodium oleate/0.02 g | Kolliphor HS15/0.2 g | Glycerin/ 2.3 g | Hydrochloric acid, sodium hydroxide/ appropriate amount | Added to a total weight of 100 g |
| 33 | 5 g | Soybean oil/1.2 g | Natural egg-yolk lecithin/ 1.2 g | Oleic acid/0.5 g Sodium oleate/0.02 g | Polysorbate 80/0.5 g | Glycerin/ 2.3 g | Citric acid, sodium citrate/ appropriate amount | Added to a total weight of 100 g |
| 34 | 5 g | Soybean oil/1.2 g | Natural egg-yolk lecithin/ 0.6 g | Oleic acid/0.5 g Sodium oleate/0.02 g | Ethanol/2 g | Glycerin/ 2.3 g | Fumaric acid, lysine/ appropriate amount | Added to a total weight of 100 g |
| 35 | 5 g | Soybean oil/1.2 g | Natural egg-yolk lecithin/ 1.2 g | Oleic acid/0.5 g Sodium oleate/0.02 g | Poloxamer 188/0.3 g | Glycerin/ 2.3 g | Citric acid, sodium citrate/ appropriate amount | Added to a total weight of 100 g |
| 36 | 5 g | Soybean oil/1.2 g | Natural egg-yolk lecithin/ 1.2 g | Oleic acid/0.1 g Sodium oleate/0.03 g | | Sucrose/ 5 g | Disodium hydrogen phosphate/ 0.023 g | Added to a total weight of 100 g |
| 37 | 5 g | Soybean oil/1.2 g | Natural egg-yolk lecithin/ 1.2 g | Oleic acid/0.3 g Sodium oleate/0.02 g | | Glucose/ 0.2 g | Disodium hydrogen phosphate/ 0.023 g | Added to a total weight of 100 g |
| 38 | 5 g | Soybean oil/1.2 g | Natural egg-yolk lecithin/ 1.2 g | Oleic acid/0.5 g Sodium oleate/0.01 g | | Sorbitol/ 0.2 g | Disodium hydrogen phosphate/ 0.023 g | Added to a total weight of 100 g |
| 39 | 5 g | Soybean oil/1.2 g | Natural egg-yolk lecithin/ 1.2 g | Oleic acid/0.5 g Sodium oleate/0.02 g | | Xylitol/ 0.2 g | Disodium hydrogen phosphate/ 0.023 g | Added to a total weight of 100 g |
| 40 | 5 g | Soybean oil/1.2 g | Natural egg-yolk lecithin/ 1.2 g | Oleic acid/0.5 g Sodium oleate/0.02 g | | Sodium chloride/ 0.2 g | Disodium hydrogen phosphate/ 0.023 g | Added to a total weight of 100 g |

(3) The formulation amounts of oil phase and water phase were weighed respectively, the oil phase was sheared for 10 min with a high-speed disperser IKA T10, and the water phase was subjected to magnetic stirring to be uniformly mixed. The water phase was warmed in a water bath of 65° C., and the oil phase was added to the water phase under the shear speed of 15000 rpm in a high-speed disperser IKA T25. After complete addition, high-speed shearing was continued for 10 min so that an initial emulsion was obtained. The pH of the initial emulsion was adjusted to 4.0 to 9.0 with a solution of a pH adjusting agent.

(4) The initial emulsion was homogenized at a pressure of 800-860 bar for 3 cycles so that a final emulsion was obtained. The finished emulsion injection was stored for stability at 25° C., and traits in appearance were observed on Day 0 and Day 30. Representative ones were observed under a microscope. The results are shown in Table 18.

1. The above Examples use corresponding pH adjusting agents for adjusting the pH to about 4.0-9.0.
2. The above Examples are supplemented to a volume of 0M mL with injectable water.

TABLE 18

| | Traits in appearance | |
|---|---|---|
| Example | Appearance on Day 0 | 25° C./Appearance on Day 30 |
| 27 | White emulsion with good fluidity | White emulsion with good fluidity |
| 28 | White emulsion with good fluidity | White emulsion with good fluidity |
| 29 | White emulsion with good fluidity | White emulsion with good fluidity |
| 30 | White emulsion with good fluidity | White emulsion with good fluidity and with oil droplets floating on the surface |
| 31 | White emulsion with good fluidity | White emulsion with good fluidity |
| 32 | White emulsion with good fluidity | White emulsion with good fluidity |
| 33 | White emulsion with good fluidity | White emulsion with good fluidity |
| 34 | White emulsion with good fluidity | White emulsion with good fluidity |
| 35 | White emulsion with good fluidity | White emulsion with good fluidity |
| 36 | White emulsion with good fluidity | White emulsion with good fluidity |
| 37 | White emulsion with good fluidity | White emulsion with good fluidity |
| 38 | White emulsion with good fluidity | White emulsion with good fluidity |
| 39 | White emulsion with good fluidity | White emulsion with good fluidity |
| 40 | White emulsion with good fluidity | White emulsion with good fluidity |

Conclusion: Except for Example 30, all the other Examples maintain good appearance under the sample retention conditions. It can be seen that the drug content of the fat emulsion may be selected from 0.1-10%. In addition, all of the stabilizers, co-emulsifiers, isosmotic adjusting agents and pH adjusting agents perform well in the formulation.

What is claimed is:

1. An ibuprofen ester derivative, a racemate, stereoisomer, or pharmaceutically acceptable salt thereof, wherein the ibuprofen ester derivative is a compound represented by Structural Formula (1):

Structural Formula (1)

N9

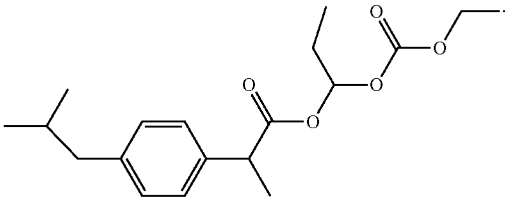

2. The ibuprofen ester derivative according to claim 1, wherein the compound represented by Structural Formula (1) is selected from a dextrorotatory enantiomer thereof, which has the following structure:

N9(S)

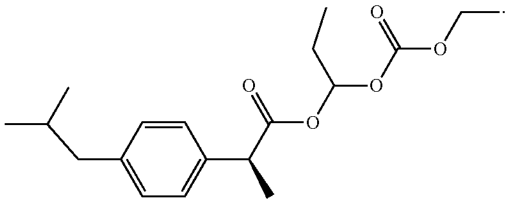

3. The ibuprofen ester derivative according to claim 2, wherein the dextrorotatory enantiomer N9(S) of the compound represented by Structural Formula (1) is a mixture of the following compounds N9(S)A and N9(S)B at any ratio:

N9(S)A

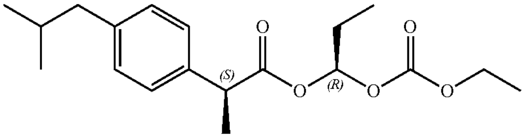

N9(S)B

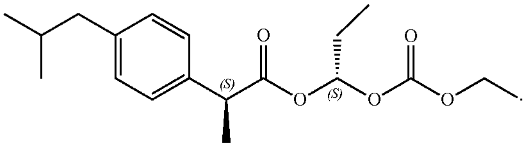

4. An emulsion preparation containing an ibuprofen ester derivative, comprising:

(a) a compound represented by Structural Formula (1), a racemate, stereoisomer, or pharmaceutically acceptable salt thereof:

Structural Formula (1)

N9

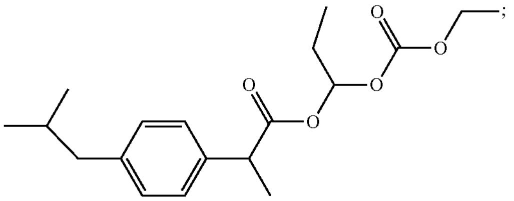

(b) an emulsifier; and (c) an oil.

5. The emulsion preparation containing an ibuprofen ester derivative according to claim 4, wherein based on a total weight of 100% of the emulsion preparation, a mass percentage of the active ingredient is 0.1-10%.

6. The emulsion preparation containing an ibuprofen ester derivative according to claim 4, wherein the compound represented by Structural Formula (1) is selected from a dextrorotatory enantiomer thereof, which has the following structure:

N9(S)

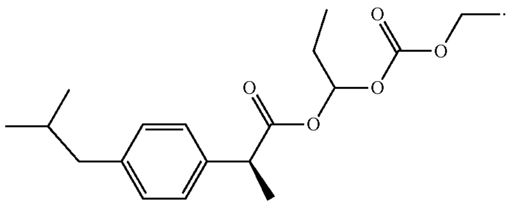

7. The emulsion preparation containing an ibuprofen ester derivative according to claim 4, wherein the emulsifier is selected from egg-yolk lecithin and/or soybean lecithin and has a mass percentage of 0.5-15%.

8. The emulsion preparation containing an ibuprofen ester derivative according to claim 4, wherein the oil is selected from one or more of sesame oil, median chain triglyceride, soybean oil, sunflower kernel oil or peanut oil and has a mass percentage of 0.1-15%.

9. The emulsion preparation containing an ibuprofen ester derivative according to claim 4, further comprising a stabilizer, wherein the stabilizer is selected from oleic acid or/and sodium oleate and has a mass percentage of 0.01-1%.

10. The emulsion preparation containing an ibuprofen ester derivative according to claim 4, further comprising an isosmotic adjusting agent, wherein the isosmotic adjusting agent is selected from one or more of sucrose, glucose, sorbitol, xylitol, sodium chloride or glycerin.

11. The emulsion preparation containing an ibuprofen ester derivative according to claim 4, further comprising a pH adjusting agent, wherein the pH adjusting agent is selected from one or more of citric acid, hydrochloric acid, citric acid, fumaric acid, lysine, tartaric acid, histidine, sodium citrate, sodium hydroxide, sodium citrate, sodium dihydrogen phosphate or disodium hydrogen phosphate.

12. The emulsion preparation containing an ibuprofen ester derivative according to claim 4, wherein the emulsion preparation is in a form of a fat emulsion injection or a nanoemulsion injection and has an average particle size within a range of 10-550 nm.

* * * * *